US006418784B1

United States Patent
Samman et al.

(10) Patent No.: US 6,418,784 B1
(45) Date of Patent: Jul. 16, 2002

(54) COMBINED COMBUSTIBLE GAS SENSOR AND TEMPERATURE DETECTOR

(75) Inventors: Amer Mohammad Khaled Samman, Dearborn; Samuel Admassu Gebremariam, Detroit; Lajos Rimai, Ann Arbor, all of MI (US)

(73) Assignee: Ford Global Technologies, Inc., Dearborn, MI (US)

( * ) Notice: Subject to any disclaimer, the term of this patent is extended or adjusted under 35 U.S.C. 154(b) by 0 days.

(21) Appl. No.: 09/415,093

(22) Filed: Oct. 8, 1999

(51) Int. Cl.[7] ...................... H01L 31/0312; G01N 27/00
(52) U.S. Cl. .................... 73/31.06; 73/25.03; 324/71.5; 257/253
(58) Field of Search ............................. 73/31.06, 31.05, 73/23.31, 25.05, 25.03; 257/414, 253; 324/71.5

(56) References Cited

U.S. PATENT DOCUMENTS

| 4,058,368 A | | 11/1977 | Svensson et al. |
| 4,300,990 A | * | 11/1981 | Maurer .................. 204/195 S |
| 4,313,338 A | | 2/1982 | Abe et al. |
| 4,878,015 A | * | 10/1989 | Schmidt et al. ............ 324/71.5 |
| 4,928,513 A | * | 5/1990 | Sugihara et al. ........... 73/25.03 |
| 4,931,851 A | | 6/1990 | Sibbald et al. |
| 4,944,273 A | | 7/1990 | Baresel et al. |
| 5,017,340 A | * | 5/1991 | Pribat et al. ................ 73/23.31 |
| 5,345,213 A | * | 9/1994 | Semancik et al. ............ 338/34 |
| 5,362,975 A | * | 11/1994 | von Windheim et al. ... 204/424 |
| 5,430,428 A | | 7/1995 | Gerblinger et al. |
| 5,656,827 A | * | 8/1997 | Kang et al. ................. 257/253 |
| 5,698,771 A | | 12/1997 | Shields et al. |
| 5,777,207 A | * | 7/1998 | Yun et al. .................. 73/31.05 |
| 5,902,556 A | | 5/1999 | Van De Vyver et al. |
| 5,948,965 A | * | 9/1999 | Upchurch et al. ......... 73/23.31 |
| 6,111,280 A | * | 8/2000 | Gardner et al. ............. 257/253 |
| 6,114,943 A | * | 9/2000 | Lauf ............................ 338/34 |
| 6,190,039 B1 | * | 2/2001 | Yaguchi ..................... 374/164 |

FOREIGN PATENT DOCUMENTS

| DE | 4008150 A1 | * | 9/1991 | |
| JP | 63128246 A | * | 5/1988 | .................. 436/16 |

* cited by examiner

Primary Examiner—Hezron Williams
Assistant Examiner—Michael Cygan
(74) Attorney, Agent, or Firm—Jennifer Stec

(57) ABSTRACT

A substrate covered with an insulating layer and a catalytic gate electrode 26 disposed on the insulating layer. The catalytic gate electrode 26 has a first end having a first contact pad 30 and a second end having a second contact pad 32. A meander 28 is placed between the first contact and the second contact. A third contact pad 24 is coupled to the underside of the substrate 22. The temperature is measured between the first contact pad 30 and second contact pad 32 while sensor's response to gas concentration is sensed between the gate electrode 26 and the third contact 24.

13 Claims, 3 Drawing Sheets

COMBINED COMBUSTIBLE GAS SENSOR AND TEMPERATURE DETECTOR

TECHNICAL FIELD

The present invention relates generally to combustible gas sensors, and more specifically, to a gas sensor in combination with a temperature detector.

BACKGROUND

Improved methods for monitoring catalysts are desired an automotive vehicles to provide accurate hydrocarbon measurements to the engine controller. Because of the high temperatures associated with catalysts the technologies available for such applications are severely limited.

Wide band gap semiconductor silicon carbide (SiC) offers advantages over conventional semiconductors such as silicon and galium arsenide for high temperature, harsh environment and high speed applications. Advances in SiC single crystal growth technology, resulting in increased wafer size of higher quality material with reduced costs has provided an area of particular interest in the development of gas sensors.

Two types of gas sensors developed using SiC technology include metal oxide semiconductors (MOS) and metal insulator semiconductors (MIS). Generally, the MOS gas sensor consists of a semiconductor substrate with an ohmic contact on one side and with the other side covered by a $SiO_2$ insulating layer with a metal gate on top. The metal gate is composed of a metal capable of catalyzing the oxidation of combustible gasses. As a result of the catalytic redox reaction on the gate surface, certain atomic and molecular species are generated which can diffuse through the porous gate to the metal gate/insulator interface where they can ionize. These ions can penetrate through the insulator thereby changing the potential distribution across the device. This changes the potential of the insulator/gate interface and thus the depletion layer inside the semiconductor which in turn shifts the voltage dependent AC admittance characteristic of the device shift along the voltage axis. For a MIS device, the DC resistance characteristics shifts along the voltage axis.

MOS and MIS sensors have an output dependent on temperature of catalytic gate. Therefore, it would be desirable to simultaneously measure temperature and the gas concentration to more accurately determine gas concentration.

SUMMARY OF THE INVENTION

The present invention combines a gas sensing structure and a temperature detecting structure within the same sensor. In one aspect of the present invention, a sensor includes a substrate and a catalytic gate electrode disposed on the substrate. The catalytic gate electrode has a first end having a first contact pad and a second end having a second contact pad. A meander is placed between the first contact and the second contact. A third contact pad is coupled to the underside of the substrate. The temperature is measured between the first contact pad and second contact pad while the gas concentration is sensed between the gate electrode and the third contact.

In a further aspect of the invention, a second meander may be placed adjacent to the first meander. The second meander may be used as a heater to heat the device. A heater may be desirable during a cold startup of the vehicle.

In yet another aspect of the invention, a method of sensing gas concentration and temperature comprises the steps of:

measuring a resistance of a meander on a substrate;

determining a temperature associated with said resistance;

measuring an electrical characteristic between the meander and a third contact on a back side of a substrate; and determining a gas concentration in response to said electrical characteristic and said temperature.

One advantage of the invention is that because the temperature of the catalytic gate is known, the output of the sensor and gas sensor may more accurately be determined. The colocation of the temperature sensor and gas sensor allows very accurate readings of the temperature at the sensor.

Other objects and features of the present invention will become apparent when viewed in light of the detailed description of the preferred embodiment when taken in conjunction with the attached drawings and appended claims.

DETAILED DESCRIPTION OF THE PREFERRED EMBODIMENT

Figure 1:
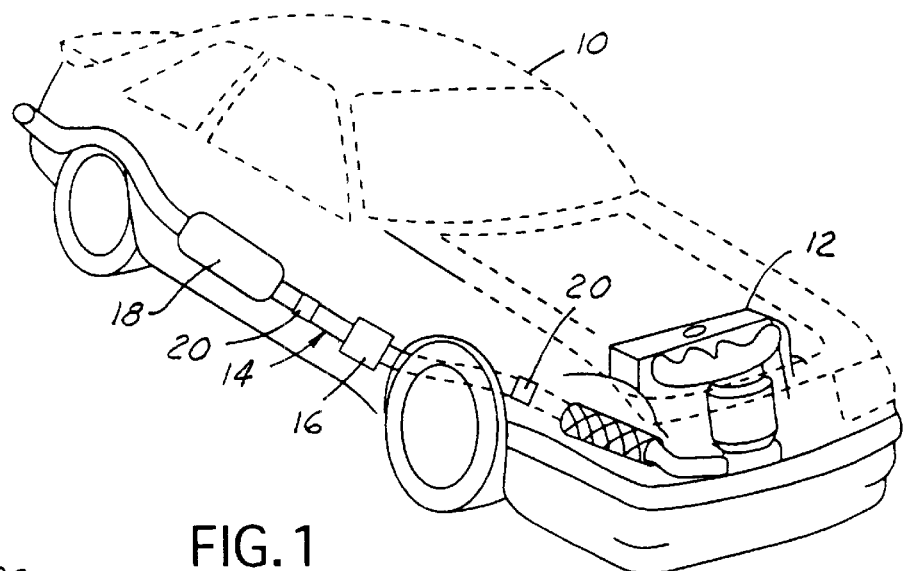
Referring now to FIG. 1, a perspective view of an automotive vehicle having a combined gas and temperature sensor according to the present invention.

In the following figures, the same reference numerals are used to identify identical components in the various views. The present invention is described with respect to a particular placement within the exhaust stream of an automotive vehicle. However, the present invention may be used in other places of the exhaust stream. Further, the present invention may be suited for other hydrocarbon detection systems such as commercial smoke stacks for buildings.

Referring now to FIG. 1, an automotive vehicle 10 has an engine 12 that generates exhaust gasses. Exhaust gasses are removed from engine 12 through an exhaust system 14. Exhaust system 14 may include a catalytic converter 16 5 and a muffler 18. During operation, catalytic converter 16 heats to a relatively high temperature to convert undesired gasses into more desirable gasses.

A sensor 20 formed according to the present invention is illustrated in two positions. The first position is between catalytic converter 16 and muffler 18. The second position is between engine 12 and catalytic converter 16. In an actual implementation, only one sensor may be used. The above two sensor embodiment would be suitable to find the amount of gas converted within catalytic converter 16. Of course, other variations and sensor positions would be evident to those skilled in the art.

Figure 2:
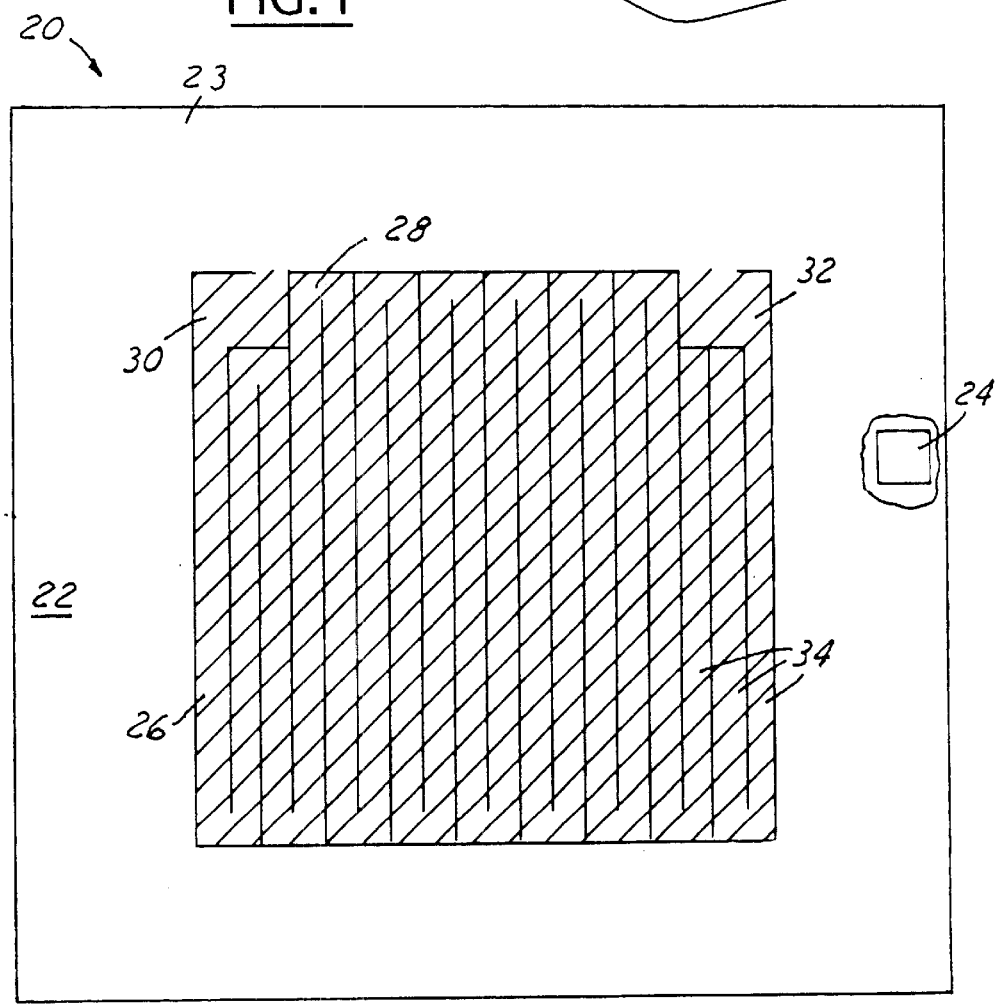
FIG. 2 is a top view of a substrate having a sensor according to the present invention.

Referring now to FIG. 2, a sensor 20 is formed on a semiconductor substrate 22. Substrate 22 is preferably SiC due to its ability to operate at temperatures in excess of 400° C. necessary for achieving catalytic oxidation-reduction of hydrocarbons as well as carbon monoxide. The preferred composition of substrate is a highly doped (approximately $10^{18}$ cm$^{-3}$) n-type SiC wafer with an approximately 3 μm thick low doping (approximately $10^{16}$ cm$^{-3}$) n-type epitaxial top layer such as those available from CREE Research or Advanced Technology Materials, Inc. An insulating layer 23 as described below may be formed on substrate 22.

A back contact 24 is positioned on the underside of substrate 22. Although illustrated as a small contact, contact 24 may extend across die under the gate electrode. Back contact 24 is formed of a metallic material and should have high thermal stability due to anticipated prolonged operation at high temperatures. Back contact 24, for example, may be formed of Pt directly on the back of substrate 22. As will be further described below, a thin layer of Ta, TaSi$_x$ or Ni may be deposited on the back of substrate 22 before back contact 24 to provide an optimum back contact ohmic characteristic.

As will be further described below, a gate electrode 26 is formed on insulating layer 23 of substrate 22.

Gate electrode 26 is comprised of a meander 28 having a first contact 30 at a first end of meander 28 and a second contact 32 positioned at a second end of meander 28. Meander 28 is shaped to substantially cover an area on substrate 22. As illustrated, meander 28 is rectangular. Meander 28 has a length associated with the distance along meander 28 between first contact 30 and second contact 32. Meander 28 is formed of a plurality of legs 34. Each leg 34 is attached to an adjacent leg at a single end. Legs 34 preferably substantially extend across the length or width of the gate electrode 26.

The temperature (T) dependent resistance R(T) of the platinum (Pt) gate electrode 26 is given by $$R(T) = \frac{L}{Wd}\rho_o[1 + \alpha(T - T_o)] = \frac{L}{W}\rho_{sh}[1 + \alpha(T - T_o)] = R_o[1 + \alpha(T - T_o)]$$

where L, W, and d are the length, width, and thickness respectively of the thin gate Pt meander 28. $\rho_o$, and $\alpha$ are the reference resistivity and the temperature coefficient of platinum, while $T_o$ is the reference temperature. For Pt, $\rho_o$=10.6 μΩ-cm and $\alpha$=0.00393 at $T_o$=20° C. For a specific Pt thickness, d and $\rho_o$ may be combined into the sheet resistance $\rho_{sh}$ in Ω/square. Then the nominal resistance $R_o$ of the gate electrode 26 is $$R_o = \frac{L}{W}\rho_{sh}$$

and the temperature sensitivity in Ω/° C. is $$dR/dT = aR_o \propto \frac{L}{W}$$

Preferably, any resistance measurement is done with a sufficiently low power to prevent heating of the catalytic gate electrode 26.

Preferably the area of gate electrode 26 is approximately 1 mm$^2$. While preferably the total die size is less than or equal to about 2 mm$^2$.

Figure 4:
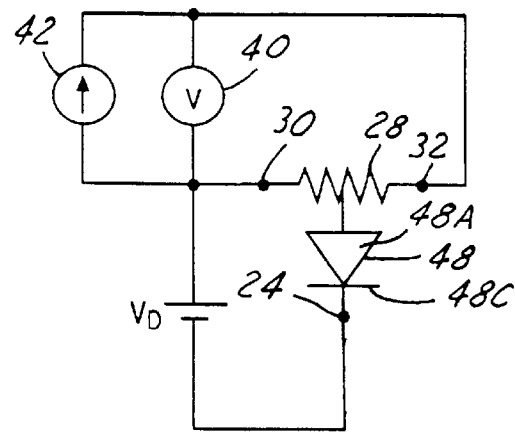
FIG. 4 is a circuit model of a MIS device according to the present invention.

Referring now to FIG. 4, the structure of the present invention can be used as a sensor in two different modes depending on the range of the gate bias: (1) In a D.C. mode by measuring the voltage across the device needed to maintain a constant forward current, or by measuring the current through the device when a constant forward voltage is applied across it; and (2) using the small signal A.C. measurement of the device capacitance when a reverse voltage is applied across it.

Figure 3:
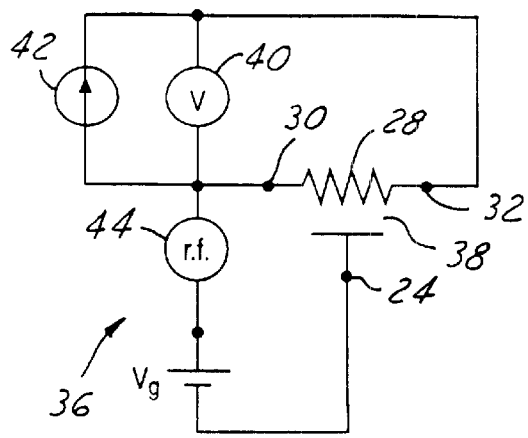
FIG. 3 is a circuit model of a MOS device according to the present invention.

The circuit model 36 depicted in FIG. 3 is the A.C. circuit. Reference numerals 24, 30 and 32 correspond respectively to the back contact 24, the first contact 30 and the second contact 32 shown in FIG. 2. A MOS capacitor 38 is formed between meander 28 and back contact 24. Voltage $V_g$ represents the gate voltage of the device. A voltage meter 40 and current source 42 are coupled in parallel with meander 28. An A.C. source 44 is coupled between meander 28 and back contact 24. Thus, the resistance of meander 28 may be measured using a D.C. voltage while the capacitance of MOS capacitor 38 may be measured using an A.C. voltage. The capacitance of MOS capacitor 38 will vary depending on the concentration of gas.

Referring now to FIG. 4, a D.C. circuit model 46 is illustrated. In this embodiment, a diode 48 is formed between meander 28 and back contact 24. In a similar manner to FIG. 3, a voltage meter 40 and current source 42 are coupled in parallel with meander 28. Diode 38 has an anode 48A that is coupled to meander 28 and a cathode 48C coupled to back contact 24. The voltage $V_d$ or the current associated therewith is dependent on the concentration of gas at meander 28.

In the operation of the device, because the temperature of the catalytic gate of the sensor may be determined at the sensor, the measured gas concentration may be adjusted for any temperature related offsets. This will enable more accurate gas concentration measurements.

Figure 5:
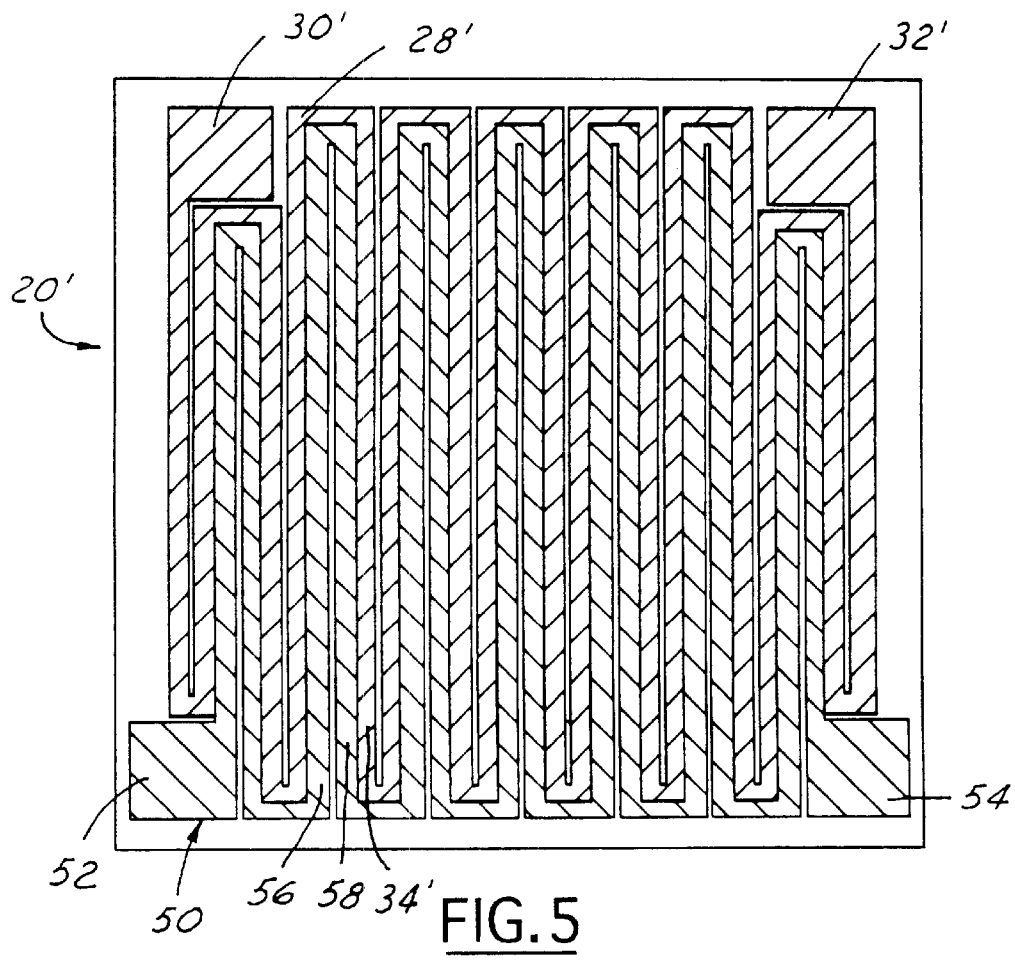
FIG. 5 is a top view of an alternative embodiment of a sensor formed according to the present invention.

Referring now to FIG. 5, a second embodiment of sensor 20' is illustrated. Sensor 20' has a meander 28' with a first contact 30' at one end and a second contact 32' at the other end. In addition to meander 28', a heater meander 50 is included thereon. Heater meander 50 has a first contact 52 at a first end and a second contact 54 at a second end. Heater 50 has a meander 56 between first contact 52 and second contact 54. Meander 56 is placed adjacent to meander 28'. Heater 50 may, for example, be used to heat sensor 20' during a cold start. Thus, it could be said that meander 56 is interwoven between meander 28. Each leg 58 of meander 56 is adjacent to a leg 34' of meander 28. Meander 56 and meander 28' are non-intersecting.

Figure 6A:
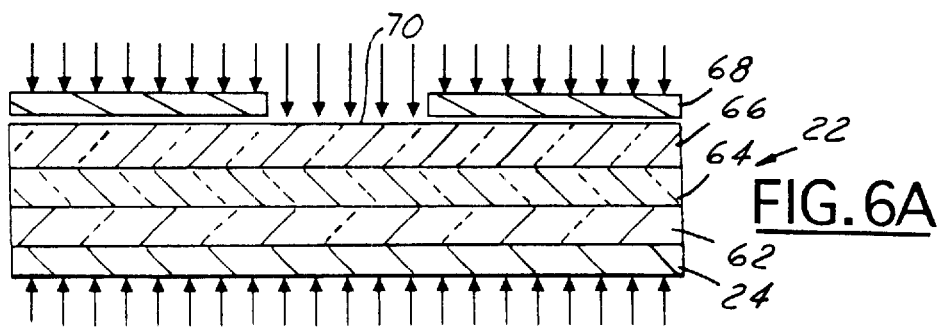
FIGS. 6A through 6D are illustrations of the fabrication of a sensor according to the present invention.

Referring now to FIG. 6A, substrate 22 as described above has a highly doped layer 62 and a lower doped layer 64. The substrate wafers are preferably thoroughly cleaned before being placed in an oxidation furnace to grow an insulating gate oxide layer. Alternatively, an aluminum nitride layer may be deposited to form insulating layer 23. A gate oxide layer 66 is grown on lower doped layer 64. Oxide layer 66 is preferably silicon oxide (SiO$_2$) or aluminum nitride (AlN). The oxide layer 66 is preferably between 300 and 500 Å thick. In the case of aluminum nitride, laser ablation may be used to deposit the aluminum nitride layer. Chemical vapor deposition may also be used.

If thermal oxidation is performed before depositing the back contact metal, oxide will form on the back side of the wafer. The back side of the wafer will need to have the oxide removed before depositing the back side contact.

A shadow mask 68 having an opening 70 may be used to deposit platinum on insulating layer 66 in the desired meander shape. Because the area of the sensor is in the millimeter range, the shadow mask is suitable. Of course, those skilled in the art would recognize that other types of masking may be used. Back contact 24 may also be formed with a shadow mask. If a heater is used, heater may be deposited similarly.

Figure 6B:
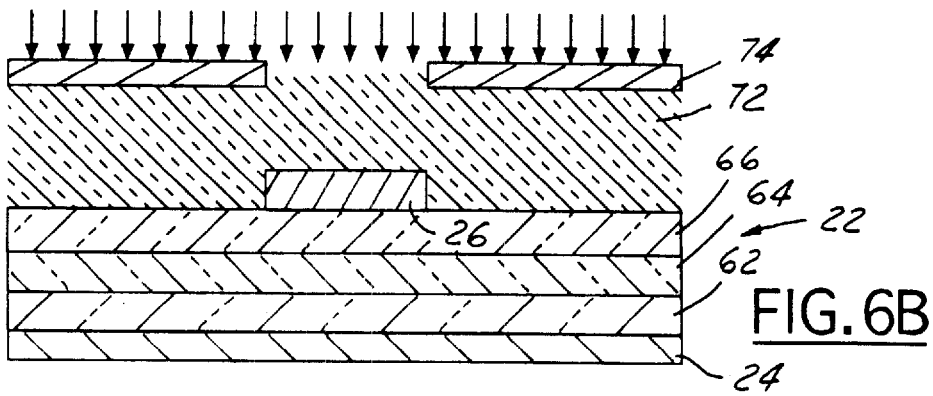

Referring now to FIG. 6B, in this manner, back contact 24 and gate electrode 26 are formed. Preferably, laser ablation is used for depositing the Pt layer.

A thick layer 72 of low temperature silicon oxide (LTO) or silicon nitride ($Si_3N_4$) is formed over oxide layer 66 and gate electrode 26. Layer 72 is used to passivate the device and provide a thick insulating base for the deposition of wire bonding contact pads. The layer 72 may be deposited at a fast growth rate by low temperature chemical vapor deposition or plasma sputtering. Although silicon oxide is a superior electrical insulator, silicon nitride provides a more resilient barrier to sodium diffusion which may prove to be a useful property in a gas sensing application.

A photolithographic step is performed to etch a window in layer 72 to expose gate electrode 26. Wet or dry etching may be used and the platinum gate electrode 26 may be used as an etch stop. A mask 74 is used in the photolithographic step.

Figure 6C:
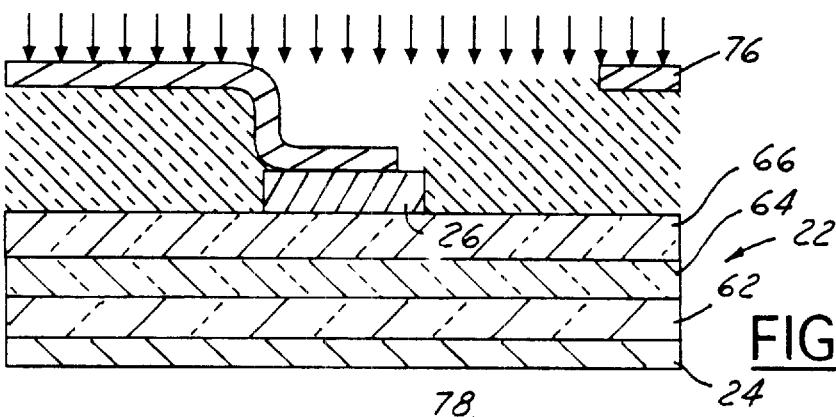

Referring now to FIG. 6C, after the layer 72 is removed over gate electrode 26, a third mask photolithography step is performed. Mask 76 partially overlaps gate 26 to provide good electrical contact between what will become a wire bonding pad and gate electrode 26. Platinum is then deposited onto the open area of mask 76 on layer 72 and onto gate electrode 26.

Figure 6D:
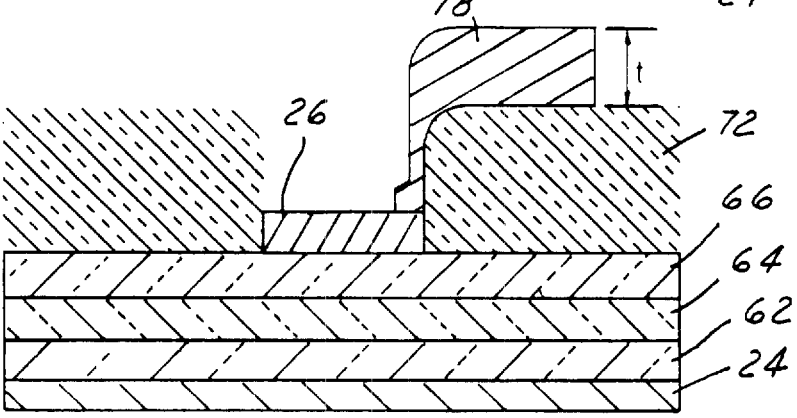

Referring now to FIG. 6D, a wire bond pad 78 is formed that is electrically coupled to gate electrode 26. Preferably, the thickness of bond pad 78 is about 1 $\mu$m that is sufficient to facilitate the wire bonding process during packaging.

The sensor 20 described above may also be integrated with a heated exhaust gas oxygen sensor for use in applications where both oxygen and combustible monitoring are desired. The benefit of the integration will decrease the total cost of the system and eliminate a second step in sensor installation at the assembly level.

While particular embodiments of the invention have been shown and described, numerous variations and alternate embodiments will occur to those skilled in the art. Accordingly, it is intended that the invention be limited only in terms of the appended claims.

What is claimed is:

1. A sensor assembly comprising:
    a semiconductor substrate;
    an insulating layer disposed on said substrate;
    a catalytic gate electrode disposed upon said substrate, said catalytic gate electrode having a first end having a first contact pad and a second end having a second contact pad, and a meander therebetween; and
    a third contact pad coupled to said substrate opposite said gate electrode,
    wherein a temperature sensor is formed comprising said first contact pad, said second contact pad and said meander therebetween;
    wherein a gas concentration dependent sensor is formed comprising said third contact pad and said meander.

2. A sensor assembly as recited in claim 1 wherein said gas dependent sensor comprises a gas concentration dependent diode.

3. A sensor assembly as recited in claim 1 wherein said gas dependent sensor comprises a gas concentration dependent capacitor.

4. A sensor assembly as recited in claim 1 further comprising a heater disposed adjacent to said first meander.

5. A sensor assembly as recited in claim 4 wherein said heater comprises a second meander interwoven and adjacent with said first meander.

6. A sensor assembly as recited in claim 1 wherein said first meander is formed of a plurality of adjacently placed legs.

7. A sensor assembly as recited in claim 1 wherein said first contact, said second contact and said first meander are formed from the group consisting of platinum, palladium, rhodium and alloys thereof.

8. A sensor assembly as recited in claim 1 wherein said substrate, said modulating layer, said catalytic gate electrode and said third contact forms a MOS capacitor sensor or a MIS diode sensor.

9. A sensor assembly as recited in claim 1 further comprising a heated exhaust gas oxygen sensor.

10. A method of sensing temperature and gas concentration comprising the steps of:
    measuring a resistance of a meander on a first side of said substrate;
    determining a temperature associated with said resistance;
    measuring an electrical characteristic between the meander and a third contact on a second side of said substrate; and
    determining a gas concentration in response to said electrical characteristic and said temperature.

11. A method of sensing as recited in claim 10 wherein said step of measuring an electrical characteristic comprises the step of measuring a capacitance between the meander and the third contact on a substrate.

12. A method of sensing as recited in claim 10 wherein said step of measuring an electrical characteristic comprises the step of measuring a resistance between the meander and the third contact on a substrate.

13. A method of sensing as recited in claim 10 wherein the step of measuring a resistance of a meander on a substrate comprises the step of applying a D.C. voltage to the meander.

* * * * *